(12) United States Patent
Zhao et al.

(10) Patent No.: US 6,608,676 B1
(45) Date of Patent: Aug. 19, 2003

(54) SYSTEM FOR DETECTING ANOMALIES AND/OR FEATURES OF A SURFACE

(75) Inventors: Guoheng Zhao, Sunnyvale, CA (US); Stanley Stokowski, Danville, CA (US); Mehdi Vaez-Iravani, Santa Clara, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 08/904,892

(22) Filed: Aug. 1, 1997

(51) Int. Cl.[7] .............................................. G01N 21/00
(52) U.S. Cl. ................ 356/237.2; 356/237.5; 356/394; 250/559.27
(58) Field of Search .................. 356/237, 239, 356/445, 375, 373, 398, 394, 237.1–237.6; 250/559.27, 559.31

(56) References Cited

U.S. PATENT DOCUMENTS

| | | | |
|---|---|---|---|
| 4,579,455 A | | 4/1986 | Levy et al. |
| 4,898,471 A | | 2/1990 | Vaught et al. |
| 4,974,927 A | | 12/1990 | Kimura |
| 5,192,856 A | | 3/1993 | Schaham |
| 5,206,699 A | | 4/1993 | Stewart et al. |
| 5,251,010 A | * | 10/1993 | Maltby, Jr. |
| 5,463,459 A | | 10/1995 | Morioka et al. |
| 5,479,259 A | | 12/1995 | Nakata et al. |
| 5,530,550 A | * | 6/1996 | Nikoonahad et al. ........ 356/614 |
| 5,576,831 A | * | 11/1996 | Nikoonahad et al. ........ 356/614 |
| 5,585,916 A | | 12/1996 | Miura et al. |
| 5,644,393 A | | 7/1997 | Nakamura et al. |
| 5,719,840 A | | 2/1998 | Jann |
| 5,737,074 A | * | 4/1998 | Haga et al. .............. 356/237.1 |
| 5,748,305 A | | 5/1998 | Shimono et al. |
| 5,864,394 A | * | 1/1999 | Jordan, III et al. ....... 356/237.3 |

FOREIGN PATENT DOCUMENTS

| | | |
|---|---|---|
| EP | 0266728 | 5/1988 |
| JP | 915163 | 1/1997 |

OTHER PUBLICATIONS

Patent Abstracts of Japan, vol. 097, No. 005, May 30, 1997 (for Japanese Patent Application No. 9–15163 noted above).
Copy of International Search Report.
"Automatic Microcircuit and Wafer Inspection," Dr. Aaron D. Gara, *Electronics Test*, May 1981, pp. 60–70.

* cited by examiner

*Primary Examiner*—Frank G. Font
*Assistant Examiner*—Sang H. Nguyen
(74) *Attorney, Agent, or Firm*—Parsons Hsue & de Runtz LLP (57) ABSTRACT

A cylindrical mirror or lens is used to focus an input collimated beam of light onto a line on the surface to be inspected, where the line is substantially in the plane of incidence of the focused beam. An image of the beam is projected onto an array of charge-coupled devices parallel to the line for detecting anomalies and/or features of the surface, where the array is outside the plane of incidence of the focused beam.

62 Claims, 8 Drawing Sheets

SYSTEM FOR DETECTING ANOMALIES AND/OR FEATURES OF A SURFACE

BACKGROUND OF THE INVENTION

This invention relates in general to surface inspection systems, and in particular, to an improved system for detecting anomalies and/or features of a surface.

The need to detect anomalies of a surface such as those on the surface of a semiconductor wafer has been recognized since at least the early 1980's. In the article "Automatic Microcircuit and Wafer Inspection in Electronics Test," May 1981, pp. 60–70, for example, Aaron D. Gara discloses a wafer inspection system for detecting whether microcircuit chips are placed upside down or not and for detecting flaws. In this system, a light beam from a laser is passed through a beam expander and a cylindrical lens having a rectangular aperture, where the lens focuses the beam to a narrow line of laser light transverse to the incidence plane of the beam to illuminate the wafer surface. It is stated in the article that the smallest defect the system can reveal is less than 10 microns wide.

The size of semiconductor devices fabricated on silicon wafers has been continually reduced. The shrinking of semiconductor devices to smaller and smaller sizes has imposed a much more stringent requirement on the sensitivity of wafer inspection instruments which are called upon to detect contaminant particles and pattern defects as well as defects of the surfaces that are small compared to the size of the semiconductor devices. At the time of the filing of this application, design rule for devices of down to 0.2 microns or below has been called for. At the same time, it is desirable for wafer inspection systems to provide an adequate throughput so that these systems can be used for in-line inspection to detect wafer defects. One type of surface inspection system employs an imaging device that illuminates a large area and images of duplicate areas of surfaces, such as a target area and a reference area used as a template, are compared to determine differences therebetween. These differences may indicate surface anomalies. Such system requires significant time to scan the entire surface of a photomask or semiconductor wafer. For one example of such system, see U.S. Pat. No. 4,579,455.

U.S. Pat. No. 4,898,471 to Stonestrom et al. illustrates another approach. The area illuminated on a wafer surface by a scanning beam is an ellipse which moves along a scan line called a sweep. In one example, the ellipse has a width of 20 microns and a length of 115 microns. Light scattered by anomalies of patterns in such illuminated area is detected by photodetectors placed at azimuthal angles in the range of 80 to 100°, where an azimuthal angle of a photodetector is defined as the angle made by the direction of light collected by the photodetector from the illuminated area and the direction of the illumination beam when viewed from the top. The signals detected by the photodetectors from a region are used to construct templates. When the elliptical spot is moved along the scan line to a neighboring region, scattered light from structures within the spot is again detected and the photodetector signal is then compared to the template to ascertain the presence of contaminant particles or pattern defects. While the scanning beam scans across the surface of the wafer, the wafer is simultaneously moved by a mechanical stage in a direction substantially perpendicular to the sweep direction. This operation is repeated until the entire surface has been inspected.

While the system of Stonestrom et al. performs well for inspecting wafers having semiconductor devices that are fabricated with coarser resolution, with a continual shrinking of the size of the devices fabricated, it is now desirable to provide an improved inspection tool that can be used to detect very small anomalies that can be difficult to detect using Stonestrom's system.

In the wafer inspection system where a light beam illuminates a small area of the surface to be inspected, such as those by Stonestrom et al. and Gara described above, the size of the illuminated spot affects the sensitivity of the system. If the spot is large relative to the size of the defects to be detected, the system will have low sensitivity since the background or noise signals may have significant amplitudes in relation to the amplitudes of the signals indicating anomalies within the spot. In order to detect smaller and smaller defects, it is, therefore, desirable to reduce the size of the illuminated area on the wafer surface.

However, as the size of the illuminated area is reduced, throughput is usually also reduced. In addition, a smaller spot size imposes a much more stringent requirement for alignment and registration. As discussed above, in many wafer inspection systems, it is common to perform a target image to a reference image comparison for ascertaining the presence of anomalies. If the area illuminated is not the intended target area but is shifted relative to the target area, the comparison may yield false counts and may become totally meaningless. Such shifting of the image relative to the intended target area is known as misregistration.

Misregistration errors can be caused by misalignment of the illumination optics due to many causes such as mechanical vibrations, as well as by change in the position of the wafer such as wafer warp or wafer tilt or other irregularities on the wafer surface. For this reason, a wafer positioning system has been proposed as in U.S. Pat. No. 5,530,550 to Nikoonahad et al. In this patent, Nikoonahad et al. propose to use the specular reflection of the scanning beam and a position sensitive detector for detecting the change in height of the wafer and use such information to alter the position of the wafer in order to compensate for a change in height or tilting of the wafer surface.

While the above-described systems may be satisfactory for some applications, they can be complicated and expensive for other applications. It is, therefore, desirable to provide an improved surface inspection system with improved sensitivity and performance at a lower cost that can be used for a wider range of applications.

SUMMARY OF THE INVENTION

One aspect of the invention is directed towards a method for detecting anomalies and/or features of a surface, comprising focusing a beam of radiation at an oblique incidence angle to illuminate a line on a surface, said beam and a direction through the beam and normal to the surface defining an incidence plane of the beam, said line being substantially in the incidence plane of the beam; and imaging said line onto an array of detectors, each detector in the array detecting light from a corresponding portion of the line.

Another aspect of the invention is directed towards a method for detecting anomalies of a surface and/or a surface feature, comprising focusing a beam of radiation at an oblique incidence angle to illuminate a line on the surface, said beam and a direction through the beam and normal to the surface defining an incidence plane of the beam; and imaging said line onto an array of detectors outside of the incidence plane, each detector in the array detecting light from a corresponding portion of the line.

Yet another aspect of the invention is directed towards an apparatus for detecting anomalies of a surface comprising means for focusing a beam of radiation at an oblique incidence angle to illuminate a line on the surface, said beam and a direction through the beam and normal to the surface defining an incidence plane of the beam, said line being substantially in the incidence plane of the beam; at least one array of detectors; and a system imaging said line onto the at least one array of detectors, each detector in the at least one array detecting light from a corresponding portion of the line.

One more aspect of the invention is directed towards an apparatus for detecting anomalies of a surface and/or a surface feature, comprising means for focusing a beam of radiation at an oblique angle to illuminate a line on the surface, said beam and a direction through the beam and normal to the surface defining an incidence plane of the beam; at least one array of detectors outside of the incidence plane; and a system imaging said line onto the array of detectors, each detector in the array detecting light from a corresponding portion of the line.

Yet another aspect of the invention is directed to an apparatus for detecting anomalies and/or a surface feature on a first and a second surface of an object, comprising means for focusing a beam of radiation at an oblique incidence angle to illuminate a line on the first surface, said beam and a direction through the beam and normal to the first surface defining an incidence plane of the beam, said line being substantially in the plane of incidence of the beam; at least one array of detectors; a system imaging said line onto the at least one array of detectors, each detector in the at least one array detecting light from a corresponding portion of the line; and means for detecting anomalies and/or a surface feature of the second surface.

One more aspect of the invention is directed to an apparatus for detecting anomalies and/or a surface feature on a first and a second surface of an object, comprising means for focusing a beam of radiation at an oblique angle to illuminate a line on the first surface, said beam and a direction through the beam and normal to the first surface defining an incidence plane of the beam; an array of detectors outside of the plane of incidence; a system imaging said line onto the array of detectors, each detector in the array detecting light from a corresponding portion of the line; and means for detecting anomalies and/or a surface feature of the second surface.

BRIEF DESCRIPTION OF THE DRAWINGS

For simplicity in description, identical components are labelled by the same numerals in this application.

DETAILED DESCRIPTION OF THE PREFERRED EMBODIMENT

Figure 1:
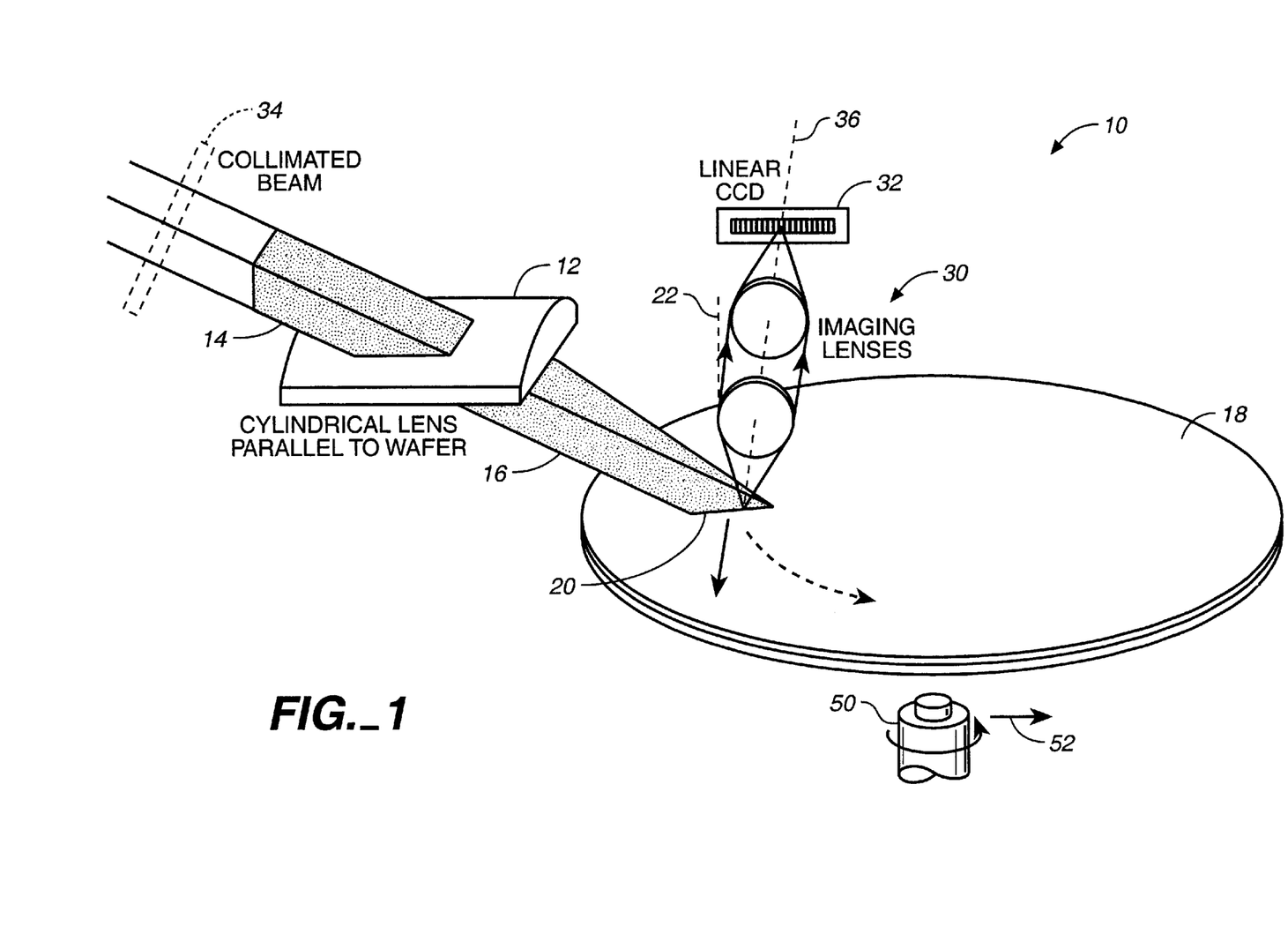
FIG. 1 is a perspective view of a surface inspection system to illustrate the preferred embodiment of the invention.

FIG. 1 is a perspective view of a surface inspection system to illustrate the preferred embodiment of the invention. System 10 includes a cylindrical objective such as a cylindrical lens 12 for focusing a preferably collimated light beam 14 to a focused beam 16 for illuminating, on surface 18 to be inspected, an area in the shape of a line 20. Beam 14 and therefore also focused beam 16 are directed at an oblique angle of incidence to the surface 18. Different from the approach by Gara described above, line 20 is substantially in the incidence plane or plane of incidence of focused beam 16. In this context, the incidence plane of beam 16 is defined by the common plane containing beam 16 and a normal direction such as 22 to surface 18 and passing through beam 16. In order for the illuminated line 20 to be in the focal plane of lens 12, cylindrical lens 12 is oriented so that its principal plane is substantially parallel to surface 18. Image of the line is focused by an imaging subsystem 30 to an array of detectors, such as a linear array of CCDs 32. The linear array 32 is preferably parallel to line 20.

In one embodiment particularly advantageous for detecting small size anomalies, the imaging subsystem 30 has an optical axis 36 which is substantially normal to line 20 so that the center portion of the linear CCD array 32 is in a plane substantially normal to the incidence plane of beam 16. The optical axis 36 may be oriented in any direction within such plane, including a position directly above the line 20. In such event, array 32 would also be directly above line 20. If desired, another array 32' shown in dotted line in FIG. 2 may be placed in a position diametrically opposite to array 32, where array 32' has optical axis 36' also substantially normal to line 20. The two arrays together may be useful to detect 45 degree line patterns.

Figure 2:
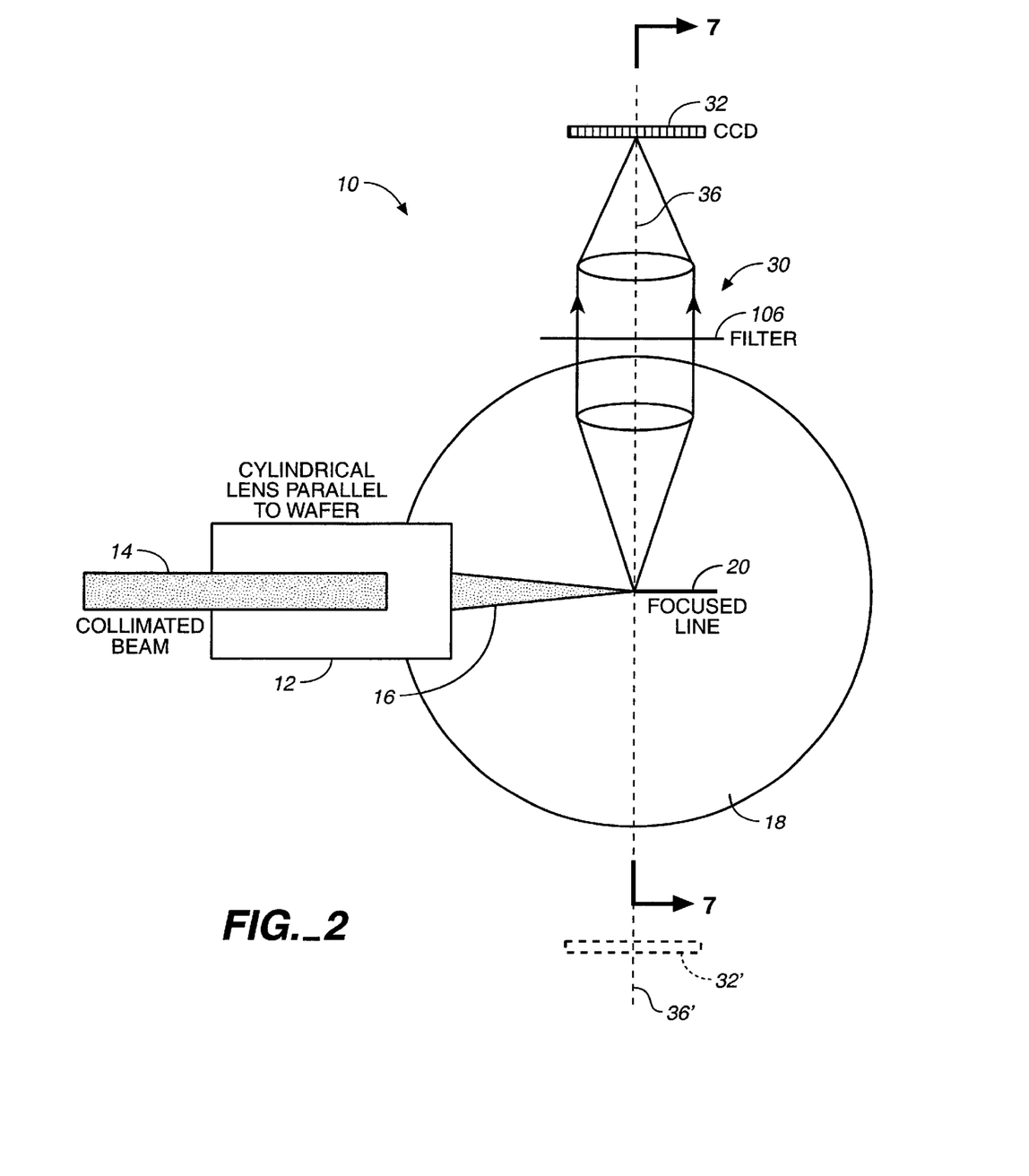
FIG. 2 is a top view of the system of FIG. 1.

The imaging subsystem 30 projects an image of a portion of the line 20 onto a corresponding detector in the CCD array 32 so that each detector in the array detects light from a corresponding portion of the line 20. The length of the line 20 is limited only by the size of the collimated input beam 14 and the physical aperture of lens or lens combination 12. In order to control the length of line 20, an optional expander 34 shown in dotted lines may be used for controlling the diameter of beam 14 so as to control the length of line 20.

Figure 3:
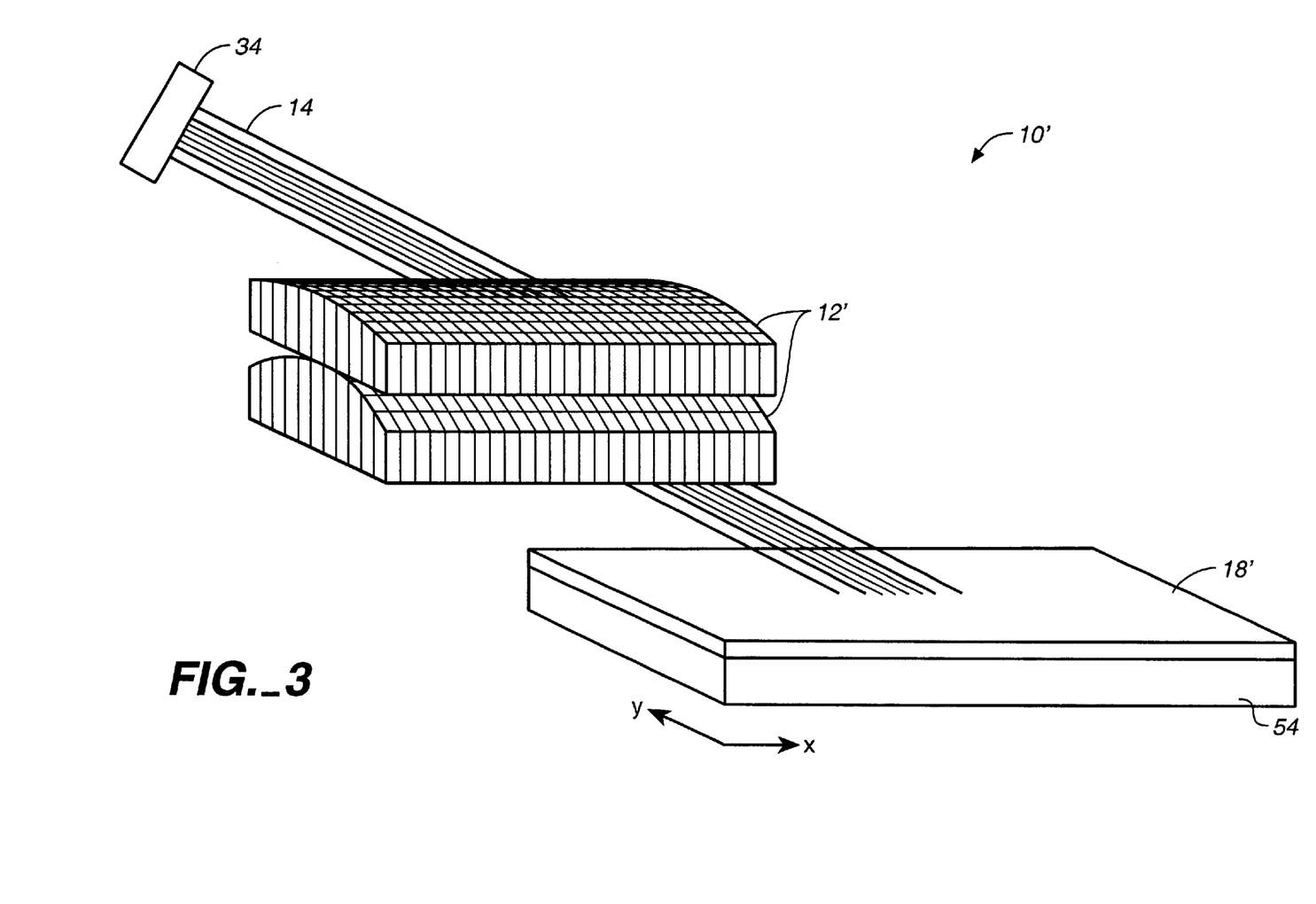
FIG. 3 is a perspective view of the illumination portion of a surface inspection system to illustrate an alternative embodiment of the invention.

FIG. 3 is a perspective view of an illumination portion of a wafer inspection system to illustrate an alternative embodiment of the invention. To simplify the diagram, the portion of the system for collecting and projecting an image of the illuminated line onto a detector array has been omitted. Instead of using a single symmetrical lens, the embodiment in FIG. 3 employs two cylindrical lenses 12' for tighter focusing, that is, focusing to a thinner line. In FIG. 1, both the illumination and collection portions of system 10 are stationary and surface 18 is rotated about a spindle 50 which is also moved along direction 52 so that line 20 scans surface 18 in a spiral path to cover the entire surface. As shown in FIG. 3, the surface 18' to be inspected can also be moved by an XY stage 54 which moves the surface along the X and Y directions in order for line 20 to scan the entire surface. Again, the illumination and collection portions of system 10' of FIG. 3 remain stationary. This is advantageous since it simplifies the optical alignment in the system, due to the fact that there is substantially no relative motion between the illumination portion and the collection portion of the system.

Figure 4:
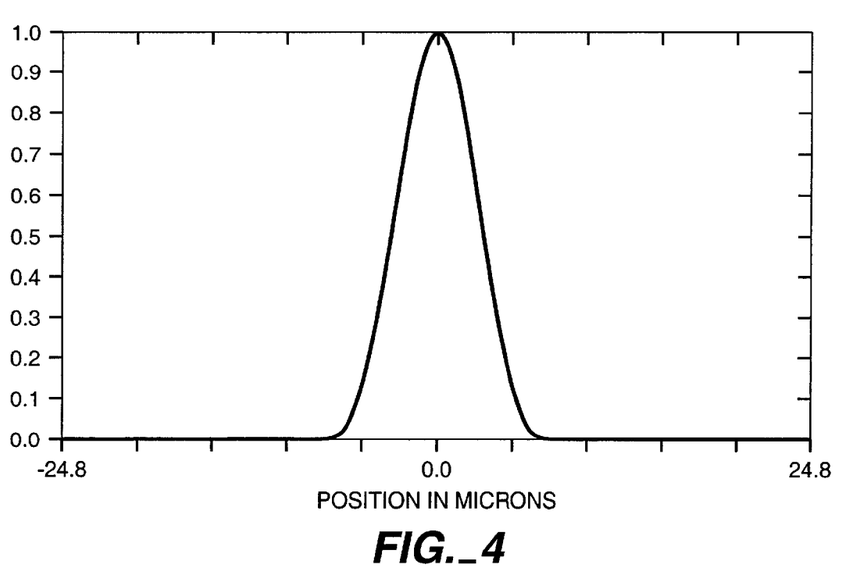
FIG. 4 is a graphical plot of a point spread function useful for illustrating the operation of the systems of FIGS. 1 and 3.

FIG. 4 is a graphical illustration of the point spread function of focused line 20 along the focused direction along any point of the line. As shown in FIG. 4, the point spread function of line 20 is Gaussian in shape, such as one which is produced if an 488 nm argon laser is used. Line 20 may also exhibit a varying point spread function along line 20 with a peak at the center of line 20. In order to avoid the variation of intensity along the line, it may be desirable to expand the beam by means of expander 34 to a longer length such as 10 mm and only use the center or central portion of the line, such as the central 5 mm of the line, so that power variation along the imaged portion of the line is insignificant. By means of an appropriate aperture in the imaging subsystem described below, it is possible to control the portion of the line imaged onto the array.

Figure 5:
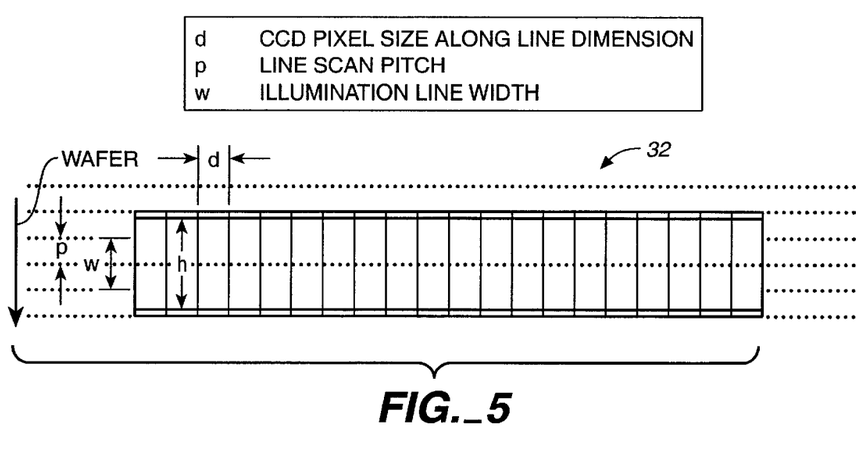
FIG. 5 is a schematic view of a parallel array of charged coupled devices (CCD) useful for illustrating the invention.

FIG. 5 is a schematic view of the linear CCD array 32. As shown in FIG. 5, the array 32 has dimension d in a direction parallel to the line 20, and W is the illumination line width. In other words, the image of line 20 as projected onto array 32 by subsystem 30 has a width of W. The pixel size of the inspection system 10 is determined by the scan pitch p and the pixel size of the detectors in the array 32 in a direction parallel to line 20, or d. In other words, the pixel size is dp. Thus, assuming that the useful portion of the illumination line projected onto the CCD array 32 has a length of 5 mm, and the illumination line width w is 10 microns and array 32 has 500 elements with d equal to 10 microns and the scan line pitch is 5 microns, the effective pixel size on the wafer is 5 microns×10 microns, assuming that the image of the line at the array has the same length as the line. In practice, to avoid aliasing, at least two or three samples are taken in each direction (along line 20 and normal to it) per effective optical spot size on the sample surface. Preferably, reasonably high quality lenses such as quality camera lenses are used, such as ones having 5 mm field of view, giving a 30° collection angle.

From the above, it is seen that system 10 has high sensitivity, since the effective "pixel" size is 5×10 microns, which is much smaller than that of Stonestrom et al. At the same time, due to the fact that the whole line of pixels on the surface 18 are illuminated and detected at the same time instead of a single illuminated spot as in Stonestrom et al., system 10 also has acceptable throughput. As noted above, the length of line 20 is limited only by the size of the collimated beam 14 and the physical aperture of lens or lens combination 12. Thus, assuming that the stage 54 has a stage speed of 10 microns per 0.1 millisecond, for a line scan rate of 10 kHz, the surface can be scanned at a speed of 100 mm per second. For a line 20 of 5 mm, the wafer surface is then scanned at a speed of 5 cm$^2$/sec.

Figure 6:
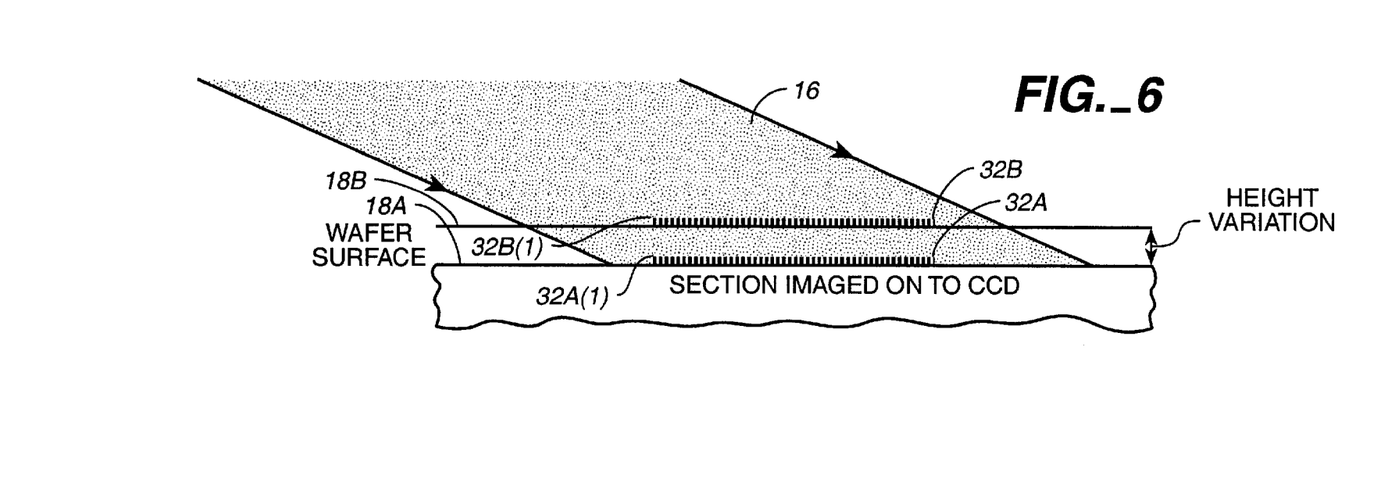
FIG. 6 is a schematic view of a light beam illuminating a line on a surface and corresponding positions of detectors of an array with respect to an imaging system along the line 6—6 in FIG. 2 to illustrate the operation of the system of FIGS. 1–3 in response to height variation of the surface inspected.
Figure 7:
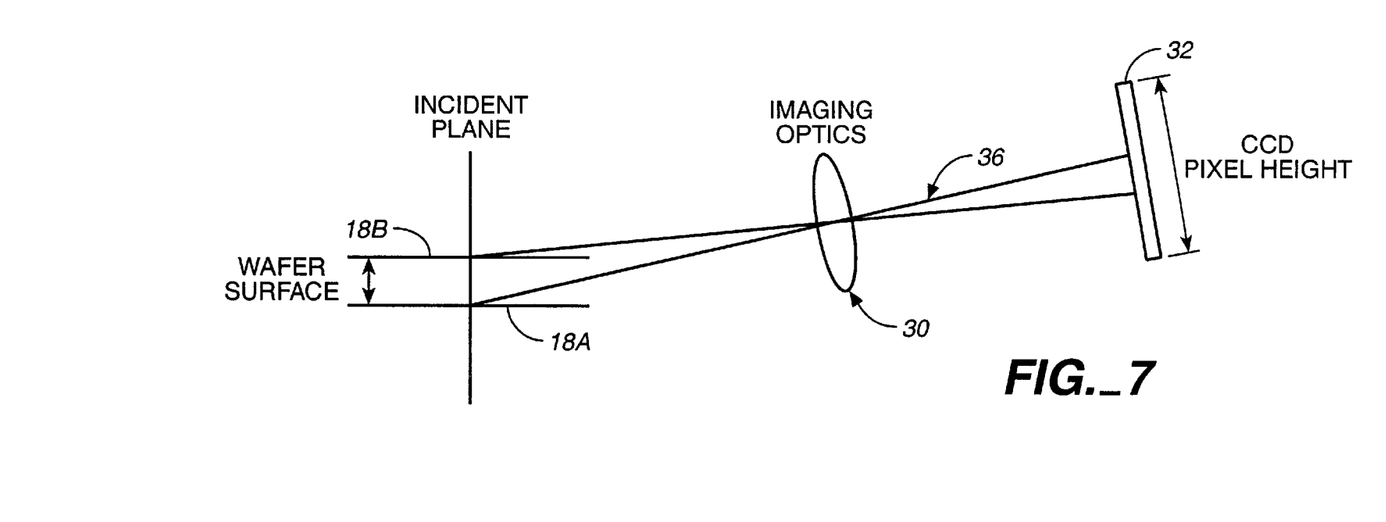
FIG. 7 is a schematic view of the imaging optics, the CCD detectors and a portion of the surface to be inspected of the system of FIG. 1 taken along the line 7—7 in FIG. 2 to illustrate the operation of the system of FIGS. 1–3 in response to height variation of the surface to illustrate the invention.

System 10 is also robust and tolerant of height variations and tilt of surface 18 and 18'. This is illustrated in reference to FIGS. 1, 2, 5–7. FIG. 6 is a cross-sectional view of a portion of the surface 18 along the line 6—6 in FIG. 2, focused beam 16 and two images of the array 32 when the surface 18 is at two different heights. FIG. 7 is a cross-sectional view of the CCD array 32, imaging subsystem 30 and two positions of a portion of the surface 18 to be inspected along the line 7—7 in FIG. 2.

In reference to FIGS. 1, 2 and 6, the imaging subsystem 30 will also project an image of the CCD array 32 onto surface 18 overlapping that of line 20. This is illustrated in FIG. 6. Thus, if surface 18 is in the position 18A, then imaging subsystem 30 will project an image 32A of the detector array on surface 18A, as shown in FIG. 6. But if the height of the surface is higher so that the surface is at 18B instead, then the imaging subsystem will project an image of the detector array at position 32B. The longer dimension of beam 16 is such that it illuminates both images 32A and 32B of the array.

From FIG. 6, it will be evident that the image of a particular detector in the array will be projected on the same portion of the surface 18 irrespective of the height of the surface. Thus, for example, the imaging subsystem 30 will project the first detector in the array 32 to position 32A(1) on surface 18A, but to the position 32B(1) on(position 18B of the surface as shown in FIG. 6. The two images are one on top of the other so that there is no lateral shift between them. In the reverse imaging direction, an image of the same portion of surface 18 and, therefore, of line 20 will be focused to two different positions on the array 32, but the two positions will also be shifted only in the vertical direction but not laterally. Hence, if the detectors cover both positions, then the variation in height between 18A, 18B of the surface will have no effect on the detection by array 32 and the system 10, 10' is tolerant of vertical height variations of the surface inspected.

One way to ensure that the array 32 covers the images of line 20 on surface 18 at both positions 18A, 18B is to choose detectors in array 32 so that the dimension of the detectors in the vertical direction is long enough to cover such change in position of the surface, so that different positions of a portion of the line 20 will be focused by subsystem 30 onto the detector and not outside of it. In other words, if the vertical dimension of the detector is chosen so that it is greater than the expected height variation of the image of the line caused by height variation of the wafer surface, the change in wafer height will not affect detection. This is illustrated in more detail in FIG. 7.

As shown in FIG. 7, the pixel height (dimension normal to optical axis and line 20) of array 32 is greater than the change in position of the image of line 20 caused by a change in wafer surface height, so that the imaging optics of subsystem 30 will project the same portion of the surface and line on the wafer surface onto the same detector. Alternatively, if the pixel height of the CCD array 32 is smaller than the expected change in position of image of line 20 due to height variation in the wafer surface, multiple rows of CCDs may be employed arranged one on top of another in a two-dimensional array so that the total height of the number of rows in the vertical direction is greater than the expected height variation of the line 20 image. If this total height is greater than the expected movement of the image of the line in the vertical direction, then such two-dimensional array will be adequate for detecting the line despite height variations of the wafer surface. The signals recorded by the detectors in the same vertical column can be simply added to give the signal for a corresponding portion of the line 20.

Even if the height or vertical dimension of array 32 is smaller than the expected height variation of the wafer surface, the imaging optics of subsystem 30 may be designed so that the change in height or vertical dimension of the projected image of line 20 onto the CCD array is within the height of the CCD array. Such and other variations are within the scope of the invention. Thus, in order for system 10 and 10' to be tolerant of wafer height variation, the image of the line at the array 32 is longer than the array, and the extent of the height variations of the image of the line 20 on the detector array is such that the projected image still falls on the detector array.

Where a two-dimensional array of detectors is employed in array 32, time delayed integration may also be performed to improve signal-to-noise or background ratio, where the shifting of the signals between adjacent rows of detectors is synchronized with the scanning of the line 20 across surface 18.

Figure 8:
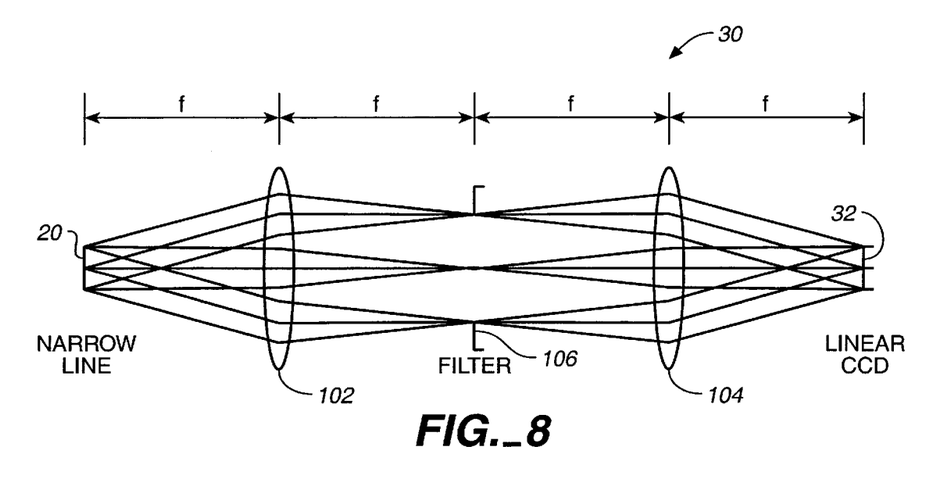
FIG. 8 is a schematic view of the collection and imaging optics in the system of FIG. 1.

FIG. 8 is a schematic view illustrating in more detail the imaging subsystem 30 of FIGS. 1 and 2. Subsystem 30 preferably comprises two identical lenses: lens 102 for collecting light from line 20 and to perform Fourier transform, and lens 104 for imaging the line onto the array 32. The two lenses 102, 104 are preferably identical to minimize aberration. A filter and polarizer may be employed at position 106 where line 20, position 106 and array 32 appear at focal points of the two lenses 102, 104 each having a focal length f. Arranged in this manner, subsystem 30 minimizes aberration. As noted above, a variable aperture may also be applied at a number of positions in subsystem 30 to control the portion of the line 20 that is focused onto array 32 by controlling the size of the aperture.

Figure 9:
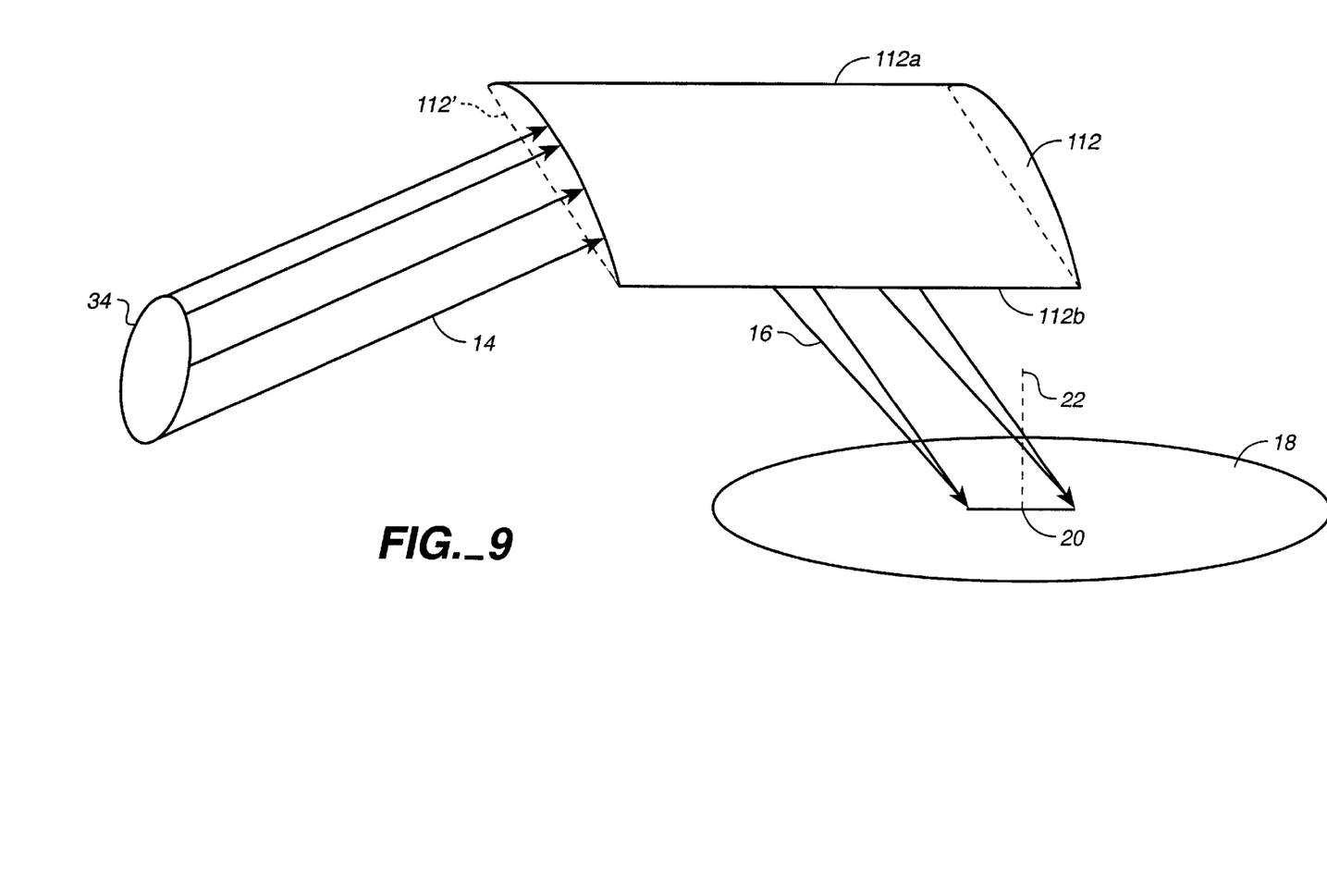
FIG. 9 is a perspective view of a portion of a wafer inspection system employing a cylindrical mirror for illustrating another alternative embodiment of the invention.

Instead of using a cylindrical lens 12 as shown in FIGS. 1 and 2, a cylindrical mirror may be used as shown in FIG. 9. In order for line 20 to appear in the focal plane of cylindrical mirror 112, the mirror should be oriented so that the plane 112' defined by and connecting the edges 112a, 112b of the mirror is substantially parallel to surface 18 inspected. In general, any cylindrical objective that has the effect of focusing a beam 14 onto a focused line on surface 18 may be used, where the focusing power is applied only in the direction substantially normal to the incidence plane defined by focus beam 16 and a normal 22 to surface 18 through the beam.

Figure 11:
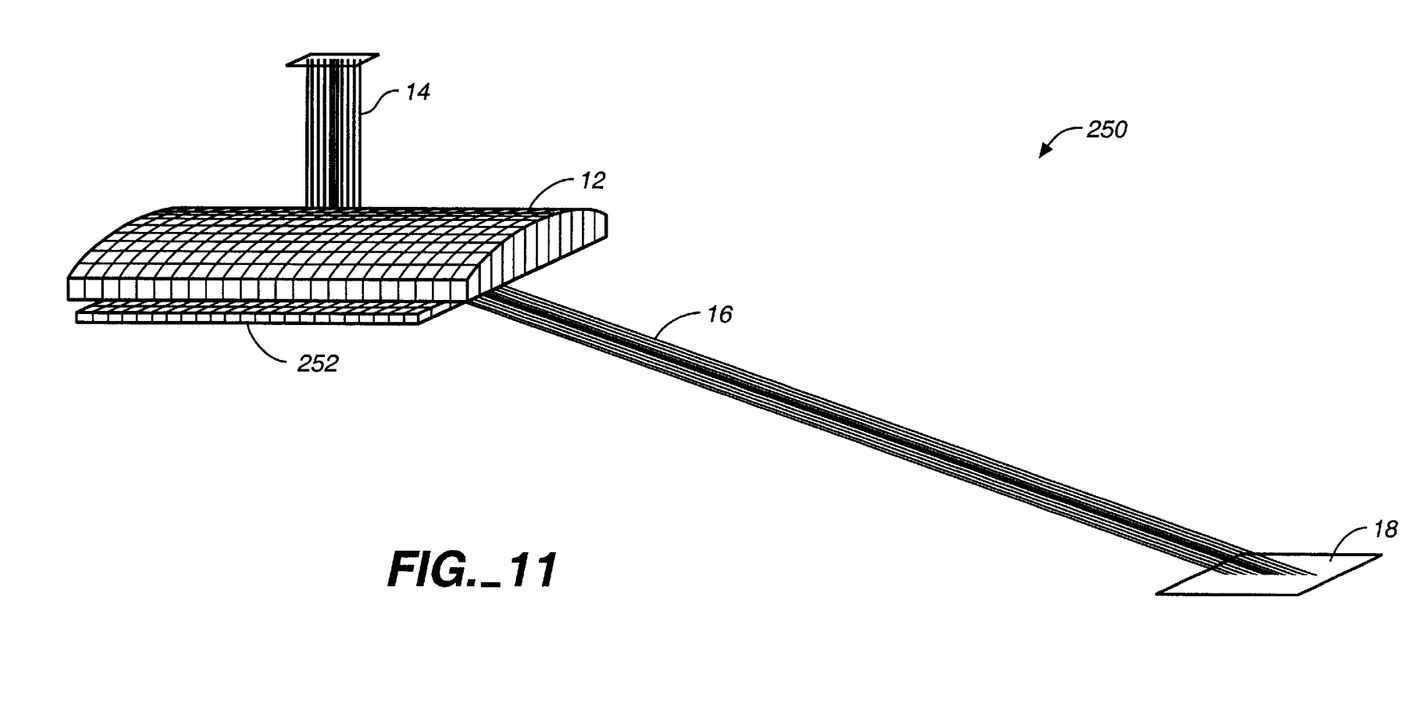
FIG. 11 is a perspective view of the illumination portion of a surface inspection system to illustrate still another alternative embodiment of the invention.

An alternative method of generating a line focus on the sample is to use a cylindrical lens in the convention way, i.e. with its principal plane perpendicular to the propagation direction of the light beam 14, and placing a diffraction grating 252 immediately following the lens. The grating period is such that main diffraction angle matches the desired illumination angle range. The lens and the grating are held parallel to each other, and to the sample surface 18. The grating line structure (or grooves) are perpendicular to the focused line direction. The grating, therefore, will only have the effect of redirecting the light along the desired incidence angle. Although a variety of different grating types can be used, it is preferable to use a holographic type grating for its enhanced efficiency.

By placing array 32 outside of the plane of incidence of beam 16 in a double dark field configuration, signal-to-noise or background ratio is improved over prior designs. A double dark field collector configuration is one where the optical axis of the collector in the subsystem is perpendicular to the optical axis of illumination and the collector lies outside the incidence plane. However, in some applications, it may be desirable to place the array in the incidence plane. Preferably, beam 16 is at an angle in the range of about 45 to 85 degrees from a normal direction to surface 18. In addition to detection of anomalies, the invention can also be used to detect other surface features such as markers.

Figure 10:
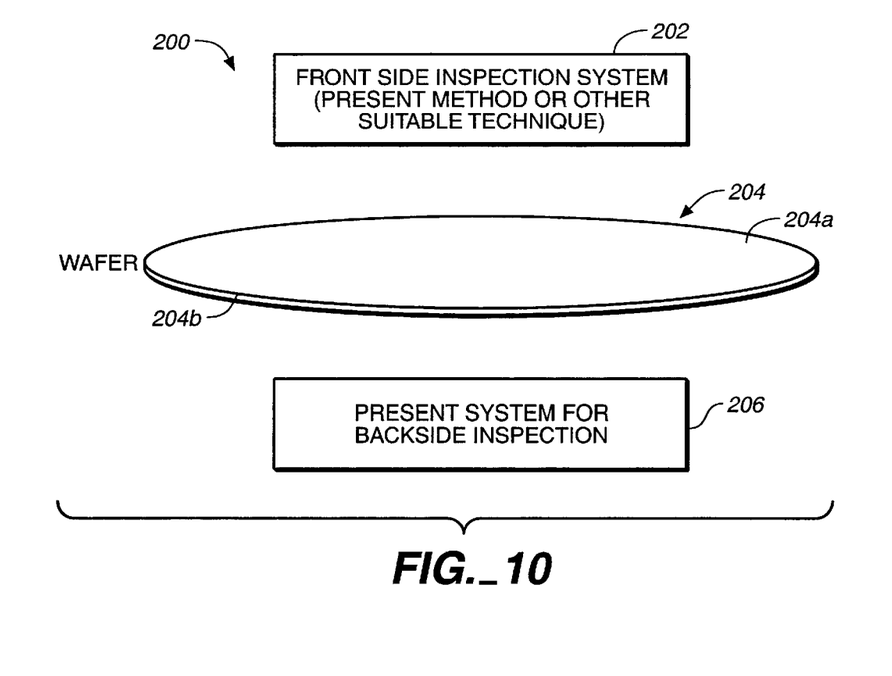
FIG. 10 is a schematic view of a system for inspecting the top and bottom surfaces of an object to illustrate another embodiment of the invention.

The invention as described above may be used to provide a viable alternate mechanism to inspect rough films, patterned or unpatterned semiconductor wafers and backsides of wafers, as well as photomasks, reticles, liquid crystal displays or other flat panel displays. The system of this invention is compact, has a simple architecture, and provides a relatively low cost alternative for inspecting patterned wafers. Furthermore, because of the low cost of the system of this invention, it may also be advantageously used in conjunction with another surface inspection system for inspecting two different surfaces of an object, as illustrated in FIG. 10. Thus, as shown in FIG. 10, a system 200 may include a front side inspection system 202 for inspecting the front side 204a of the semiconductor wafer 204, and a system 206 (which may be similar to that in FIGS. 1, 2 or 3) for inspecting the backside 204b of the wafer. If, as in the invention described above, the illumination and light collection portions of the system remain stationary and the surface 204b is inspected by moving the surface, the two systems 202, 206 may need to be synchronized. System 202 may include a system such as that described above in reference to FIGS. 1–3, or may be one of many different kinds of anomaly and surface feature inspection systems. All such variations are within the scope of the invention.

While the invention has been described by reference to various embodiments, it will be understood that modification changes may be made without departing from the scope of the invention which is to be defined only by the appended claims or their equivalents.

What is claimed is:

1. A method for detecting anomalies and/or features of a surface, comprising:
   focusing a beam of radiation into a focused beam at an oblique incidence angle to a focused line on the surface, said beam and a direction that is through the beam and that is normal to the surface defining an incidence plane of the beam, said line being substantially in the plane of incidence of the beam; and
   imaging said line onto an array of detectors, each detector in the array detecting radiation from a corresponding portion of the line.

2. The method of claim 1, said imaging being such that an image of the line at said array is longer than the array.

3. The method of claim 1, wherein said imaging images a center part of the line onto said array.

4. The method of claim 1, wherein said focusing focuses the beam of radiation substantially only in a direction normal to the plane of incidence.

5. The method of claim 4, said focusing comprising passing a beam of radiation through a cylindrical lens or to a cylindrical mirror.

6. The method of claim 1, further comprising controlling a cross-sectional dimension of the beam of radiation and said oblique incidence angle in order to select length of the illuminated line.

7. The method of claim 6, said controlling comprising expanding a beam of radiation so that the beam has a desired diameter after expansion.

8. The method of claim 1, wherein said imaging focuses the line along an axis that is substantially normal to the line.

9. The method of claim 1, said imaging employing a variable aperture, said method further comprising controlling the aperture of the variable aperture in response to roughness of the surface.

10. The method of claim 1, further comprising causing relative motion between the surface and the beam so that the line scans the surface to detect anomalies and/or a surface feature.

11. The method of claim 10, wherein said causing moves the surface and leaves the beam and the array substantially stationary.

12. The method of claim 1, said oblique angle being in a range of about 45 to 85 degrees from a normal direction to the surface.

13. The method of claim 1, wherein said imaging employs an objective, and wherein the line is in a focus plane of the objective.

14. The method of claim 1, further comprising performing time delayed integration at the array of detectors.

15. The method of claim 1,
wherein said imaging images said line onto an array of detectors outside of the plane of incidence.

16. The method of claim 1, wherein said imaging causes an image of said line to fall onto said array of detectors despite changes in position of the surface.

17. The method of claim 1, wherein said focusing focuses the beam to a thin line on the surface.

18. The method of claim 1, wherein said focusing focuses a collimated beam into the focused beam.

19. The method of claim 1, wherein said focused line has a substantially uniform width.

20. An apparatus for detecting anomalies of a surface, comprising:
optics focusing a beam of radiation into a focused beam at an oblique incidence angle to a focused line on the surface, said beam and a direction that is through the beam and that is normal to the surface defining an incidence plane of the beam, said line being substantially in the plane of incidence of the beam;
at least one array of detectors; and
a system imaging said line onto the at least one array of detectors, each detector in the at least one array detecting radiation from a corresponding portion of the line.

21. The apparatus of claim 20, wherein an image of the line formed by the system at the array is longer than the array.

22. The apparatus of claim 20, wherein said system images a center part of the line onto said array.

23. The apparatus of claim 20, said optics focusing the beam substantially only in a direction normal to the plane of incidence.

24. The apparatus of claim 23, said optics comprising a cylindrical lens or a cylindrical mirror.

25. The apparatus of claim 24, said optics Using a cylindrical lens that has a principal plane substantially parallel to the surface.

26. The apparatus of claim 25, wherein said optics focuses an input radiation beam directed at the optics, said input beam being substantially normal to the surface and to the lens, said optics further comprising a diffraction grating for redirecting radiation from the lens towards the surface at an oblique angle to the surface.

27. The apparatus of claim 25, wherein said optics focuses an input radiation beam directed at the optics, said input beam being in a direction oblique to the surface and to the principal plane of the lens.

28. The apparatus of clam 24, said optics comprising a cylindrical mirror that has two substantially straight edges, wherein a plane defined by the two edges is substantially parallel to the surface.

29. The apparatus of claim 24, said optics focusing a collimated beam into the focused beam.

30. The apparatus of claim 24, when said focused line has a substantially uniform width.

31. The apparatus of claim 20, further comprising an expander expanding the beam of radiation prior to focusing by the optics.

32. The apparatus of claim 20, wherein said at least one array of detectors is outside of the plane of incidence.

33. The apparatus of claim 20, wherein said system has an optical axis that is substantially normal to the line.

34. The apparatus of claim 20, said system comprising a variable aperture for varying a collection angle of the system.

35. The apparatus of claim 20, further comprising means for causing relative motion between the surface and the beam so that the line scans the surface to detect anomalies and/or a surface feature.

36. The apparatus of claim 35, said at least one array of detectors being substantially stationary relative to the beam when relative motion is caused between the surface and the beam.

37. The apparatus of claim 20, said oblique angle being in a range of about 45 to 85 degrees from a normal direction to the surface.

38. The apparatus of claim 20, said at least one array of detectors being a linear array substantially parallel to the line.

39. The apparatus of claim 20, said system comprising lens means having a Fourier plane, said apparatus further comprising a filter and polarizer substantially in the Fourier plane.

40. The apparatus of claim 20, wherein said array of detectors is outside of the plane of incidence.

41. The apparatus of claim 20, wherein a dimension of said away and/or imaging by said system causes an image of said line to fall onto said array of detectors despite changes in position of the surface.

42. The apparatus of claim 41, wherein a dimension of said array in a direction transverse to the line is such that an image of said line falls onto said array of detectors despite changes in position of the surface.

43. The apparatus of claim 41, wherein imaging by said system causes an image of said line to fall onto said array of detectors despite changes in position of the surface.

44. The apparatus of claim 20, wherein said optics focuses the beam to a thin line on the surface.

45. An apparatus for detecting anomalies and/or a surface feature on a first and a second surface of an object, comprising:
optics focusing a beam of radiation into a focused beam at an oblique incidence angle to a focused line on the first surface, said beam and a direction that is through the beam and that is normal to the first surface defining an incidence plane of the beam, said line being substantially in the plane of incidence of the beam;
at least one array of detectors;
a system imaging said line onto the at least one array of detectors, each detector in the at least one array detecting radiation from a corresponding portion of the line; and
means for detecting anomalies and/or a surface feature of the second surface.

46. The apparatus of claim 45, said first and second surfaces being on opposite sides of the object.

47. The apparatus of claim 45, wherein said array of detectors is outside of the plane of incidence.

48. The apparatus of claim 45, wherein said optics focuses the beam to a thin line on the first surface.

49. The apparatus of claim 45, said optics focusing a collimated beam into the focused beam.

50. The apparatus of claim 45, wherein said focused line has a substantially uniform width.

51. A method for detecting anomalies and/or features of a surface, comprising:

focusing a beam of radiation into a focused beam at an oblique incidence angle to a focused line on the surface, said beam and a direction that is through the beam and that is normal to the surface defining an incidence plane of the beam, said focused line being substantially in the plane of incidence of the beam; and imaging said line onto an array of detectors.

52. The method of claim 51, wherein each of at least some of the detectors in the array detects radiation from a corresponding portion of the line.

53. The method of claim 51, wherein said focusing focuses a collimated beam into the focused beam.

54. The method of claim 51, wherein said focused line has a substantially uniform width.

55. An apparatus for detecting anomalies and/or features of a surface, comprising:

optics focusing a beam of radiation into a focused beam at an oblique incidence angle to a focused line on the surface, said beam and a direction that is trough the beam and that is normal to the surface defining an incidence plane of the beam, said focused line being substantially in the plane of incidence of the beam; and a system imaging said line onto an array of detectors.

56. The apparatus of claim 55, said apparatus comprising said array of detectors, wherein each of at least some of the detectors in the array detects radiation from a corresponding portion of the line.

57. The apparatus of claim 53, said optics focusing a collimated beam into the focused beam.

58. The apparatus of claim 55, wherein said focused line has a substantially uniform width.

59. An apparatus for detecting anomalies and/or features of a surface, comprising:

means for focusing a beam of radiation into a focused beam at an oblique incidence angle to a focused line on the surface, said beam and a direction that is through the beam and that is normal to the surface defining an incidence plane of the beam, said focused line being substantially in the plane of incidence of the beam;

detector means; and means for imaging said line onto said detector means.

60. The apparatus of claim 59, said detector means comprising an array of detectors wherein each of at least some of the detectors in the array detects radiation from a corresponding portion of the line.

61. The apparatus of claim 59, wherein said means for focusing focuses a collimated beam into the focused beam.

62. The apparatus of claim 59, wherein said focused line has a substantially uniform width.

* * * * *